United States Patent
Dell'Oca et al.

(10) Patent No.: US 9,949,796 B2
(45) Date of Patent: Apr. 24, 2018

(54) ROUND DEPTH GAUGE

(71) Applicant: SYNTHES USA, LLC, West Chester, PA (US)

(72) Inventors: Alberto Fernandez Dell'Oca, Montevideo (UY); Glen Pierson, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 503 days.

(21) Appl. No.: 13/728,064

(22) Filed: Dec. 27, 2012

(65) Prior Publication Data
US 2013/0172897 A1    Jul. 4, 2013

Related U.S. Application Data

(60) Provisional application No. 61/582,025, filed on Dec. 30, 2011, provisional application No. 61/721,041, filed on Nov. 1, 2012, provisional application No. 61/598,922, filed on Feb. 15, 2012.

(51) Int. Cl.
| | |
|---|---|
| *A61B 5/107* | (2006.01) |
| *A61B 19/00* | (2006.01) |
| *A61B 5/00* | (2006.01) |
| *A61B 90/00* | (2016.01) |

(52) U.S. Cl.
CPC ............ *A61B 19/46* (2013.01); *A61B 5/1072* (2013.01); *A61B 5/4504* (2013.01); *A61B 90/06* (2016.02); *A61B 2090/061* (2016.02)

(58) Field of Classification Search
CPC ................... A61B 2019/461; A61B 2019/462
See application file for complete search history.

(56) References Cited

U.S. PATENT DOCUMENTS

| 517,073 A | 3/1894 | Sloane |
|---|---|---|
| 1,327,114 A | 1/1920 | Rhein |
| 3,964,170 A | 6/1976 | Zbarsky |
| 4,033,043 A | 7/1977 | Cunningham |
| 4,238,885 A | 12/1980 | Lendi et al. |
| 4,312,363 A | 1/1982 | Rothfuss et al. |
| 5,013,318 A | 5/1991 | Spranza, III |
| 5,409,493 A | 4/1995 | Greenberg |
| 5,620,449 A | 4/1997 | Faccioli et al. |
| 6,295,671 B1 | 10/2001 | Reesby et al. |
| 6,802,817 B2 | 10/2004 | Baxter-Jones et al. |

(Continued)

FOREIGN PATENT DOCUMENTS

| CN | 101166465 | 4/2008 |
|---|---|---|
| CN | 101677784 | 3/2010 |

(Continued)

*Primary Examiner* — Samuel Hanna
(74) *Attorney, Agent, or Firm* — Fay Kaplun & Marcin, LLP (57) ABSTRACT

A device for measuring blind holes formed through a bone includes (a) a first elongated rod including a shaft extending from a proximal end to a distal end, the distal end including an increased diameter abutment extending radially outward therefrom, the abutment including a proximal surface formed to contact a portion of the bone adjacent a distal opening of the blind hole to assume a locked configuration with the bone and (b) a second elongated rod extending from a proximal end to a distal end along a longitudinal axis.

11 Claims, 11 Drawing Sheets

(56) References Cited

U.S. PATENT DOCUMENTS

| | | | |
|---|---|---|---|
| 7,101,181 | B2 | 9/2006 | Bompard et al. |
| 7,134,216 | B2 | 11/2006 | Rupp et al. |
| 7,293,364 | B2 | 11/2007 | Dace et al. |
| 7,559,150 | B2 | 7/2009 | Fernandez |
| 7,823,296 | B2 | 11/2010 | Dell'Oca |
| 7,976,550 | B2 | 7/2011 | Trudeau |
| 2002/0104230 | A1* | 8/2002 | White ............... G01B 3/28 33/755 |
| 2005/0066535 | A1 | 3/2005 | Rupp et al. |
| 2006/0207118 | A1 | 9/2006 | Kim |
| 2006/0207119 | A1 | 9/2006 | Kim et al. |
| 2006/0224161 | A1* | 10/2006 | Bhattacharyya ....... A61B 19/46 606/102 |
| 2007/0088366 | A1* | 4/2007 | Fernandez ............. A61B 5/103 606/102 |
| 2007/0227023 | A1 | 10/2007 | Dace et al. |
| 2008/0039860 | A1 | 2/2008 | Trudeau |
| 2008/0306408 | A1 | 12/2008 | Lo |
| 2009/0005786 | A1 | 1/2009 | Prien et al. |
| 2009/0049705 | A1 | 2/2009 | Kim |
| 2009/0157088 | A1* | 6/2009 | Mengato ................ A61B 90/06 606/102 |
| 2009/0272001 | A1 | 11/2009 | Dell'Oca |
| 2009/0326533 | A1 | 12/2009 | Dell'Oca |
| 2010/0154238 | A1 | 6/2010 | Harshbarger et al. |
| 2010/0228350 | A1* | 9/2010 | Gornet ................... A61F 2/442 623/17.16 |
| 2012/0191104 | A1 | 7/2012 | Jost et al. |

FOREIGN PATENT DOCUMENTS

| | | |
|---|---|---|
| CN | 201578245 | 9/2010 |
| CN | 101874737 | 11/2010 |
| CN | 201879693 | 6/2011 |
| CN | 201920730 | 8/2011 |
| DE | 200 11 156 U 1 | 1/2001 |
| EP | 1 938 039 | 7/2008 |
| JP | S55-3000 | 1/1980 |
| JP | S56-121537 | 9/1981 |
| WO | 2007/047466 | 4/2007 |

* cited by examiner

ROUND DEPTH GAUGE

PRIORITY CLAIM

The present application claims priority to U.S. Provisional Appln. Ser. No. 61/582,025 entitled "Round Depth Gauge" filed on Dec. 30, 2011, U.S. Provisional Appln. Ser. No. 61/721,041 entitled "Depth Gauge I" filed on Nov. 1, 2012 and U.S. Provisional Appln. Ser. No. 61/598,922 entitled "Single Patient Use Depth Gauge" filed on Feb. 15, 2012, the entire disclosures of which are incorporated herein by reference.

BACKGROUND

Bone fixation procedures often require the insertion of a bone screw transversely though a bone. In such cases, it is necessary to assess the depth of a hole formed through the bone. Existing measurement devices include a calibrated rod having a single hook provided on an end thereof. In operation, the rod is inserted through the bone hole and, after emerging from an opposing end of the bone hole, the rod is retracted until it abuts against a blind edge adjacent the opposing end. The disadvantage of such devices is that hooking the edge of the bone hole is quite difficult, especially when measuring smaller diameter holes. There is a need for a hole-depth measuring instrument that provides a fast and accurate measurement. There is a further need for a measuring instrument which firmly engages the opposing distal edge of the bone hole to allow for a precise measurement of the bone hole.

SUMMARY OF THE INVENTION

The present invention is directed to a device for measuring blind holes formed through a bone and comprises a first elongated rod including a shaft extending from a proximal end to a distal end, the distal end including an increased diameter abutment extending radially outward therefrom, the abutment including a proximal surface formed to contact a portion of the bone adjacent a distal opening of the blind hole to assume a locked configuration with the bone. The device according to the invention further comprises a second elongated rod extending from a proximal end to a distal end along a longitudinal axis.

DETAILED DESCRIPTION

The present invention may be further understood with reference to the following description and the appended drawings, wherein like elements are referred to with the same reference numerals. The present invention relates to the measurement of holes drilled through a bone in accordance with a bone fixation procedure for a fractured or otherwise damaged bone. Exemplary embodiments of the present invention describe a probe for insertion through a hole drilled through the bone to provide a simple and effective tool for measuring the depth of a blind hole. The probe according to the invention includes first and second elongated, substantially cylindrical rods. The first rod includes an elongated shaft and an abutment at a distal end thereof with a diameter greater than that of a portion of the shaft extending proximally therefrom. The diameter of the abutment is smaller than the diameter of the blind hole to permit insertion of the abutment therethrough. The second rod includes an elongated shaft having an increased diameter insert at a distal end thereof. The insert includes a groove extending thereinto to slidably receive the shaft of the first rod. In an operative configuration, the first rod is slidably received within the groove of the second rod. The probe is then positioned against a proximal opening of the hole formed through a bone. The first rod is then moved distally relative to the second rod to pass the abutment through the hole and out of a distal side of the bone. Once the abutment has moved distally through the distal opening of the hole, the second rod is moved distally relative to the first rod through the bone out the distal opening of the hole until engagement of the insert with the abutment prevents further distal movement thereof. In this configuration, the combined diameter of the abutment and the insert prevents proximal retraction of the probe out of the hole. Specifically, in this operative configuration, a combined diameter of a portion of the first and second rods positioned proximally of the abutment is smaller than the diameter of the blind hole. In the operative configuration, the abutment projects radially outward beyond the edge of the blind hole so that the abutment is physically prevented from being withdrawn into the blind hole. The first and second rods are then moved proximally until the abutment is seated against a portion of the bone adjacent the distal opening. A substantially cylindrical housing provided over proximal portions of the first and second rods is then moved distally until a distal end of the housing is seated against a proximal opening of the hole. In this configuration, markings provided on one or both of the first and second rods indicate the depth of insertion of the probe into the bone and, consequently, a length of the hole formed in the bone. The exemplary probe according to the invention permits the abutment to firmly engage a distal edge of the bore, allowing for precise measurement of the depth of the blind hole. It should be noted that the terms "proximal" and "distal" as used herein, refer to a direction toward (proximal) and away from (distal) a user of the device.

Figure 1:
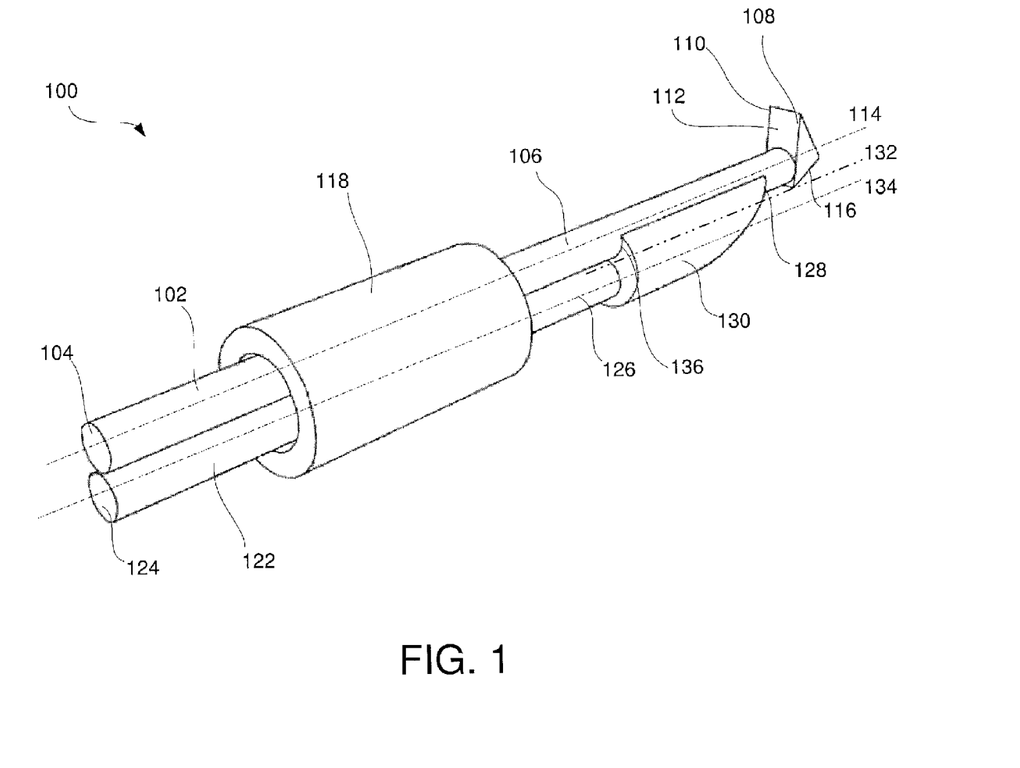
FIG. 1 shows a perspective view of a depth gauge probe according to an exemplary embodiment of the invention.
Figure 2:
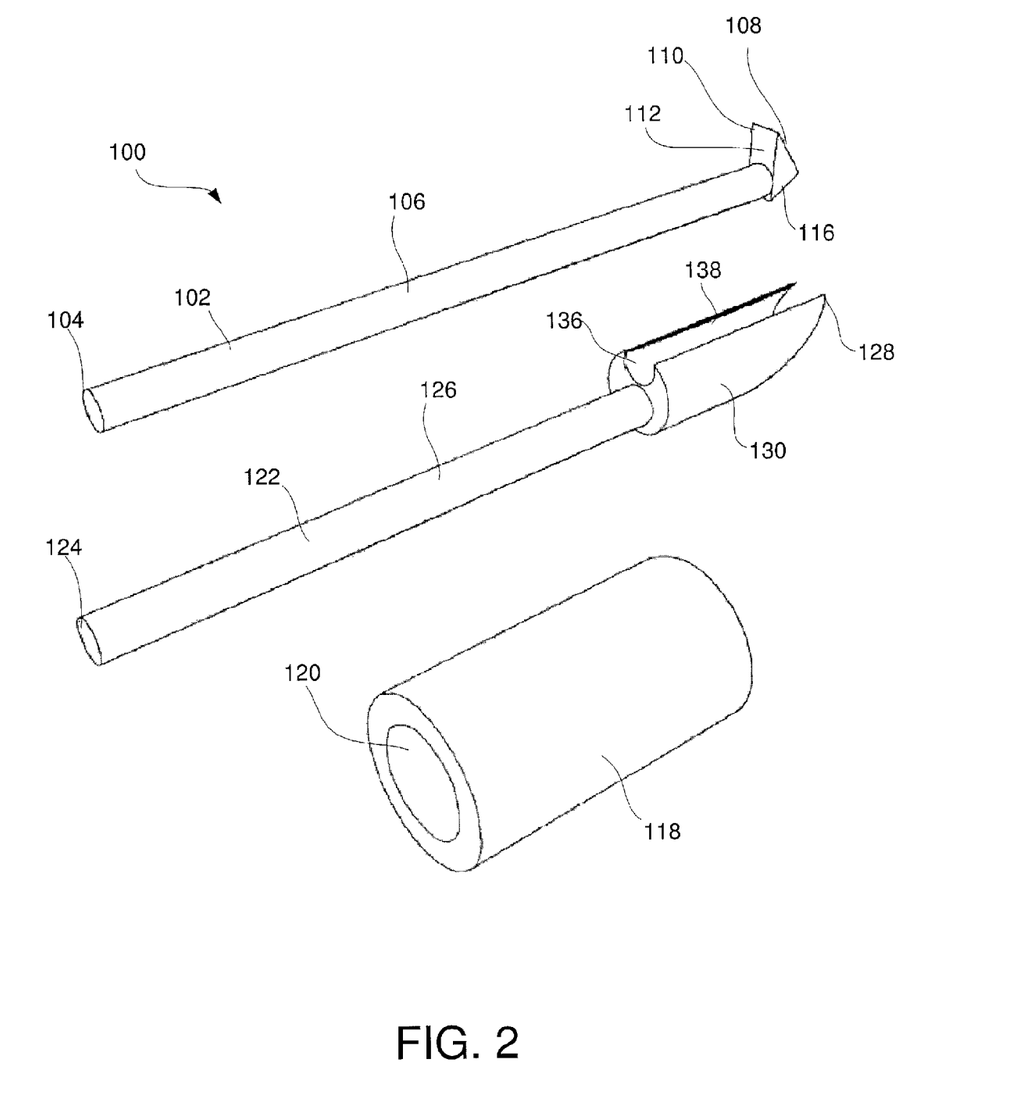
FIG. 2 shows an exploded view of the depth gauge of FIG. 1.
Figure 3:
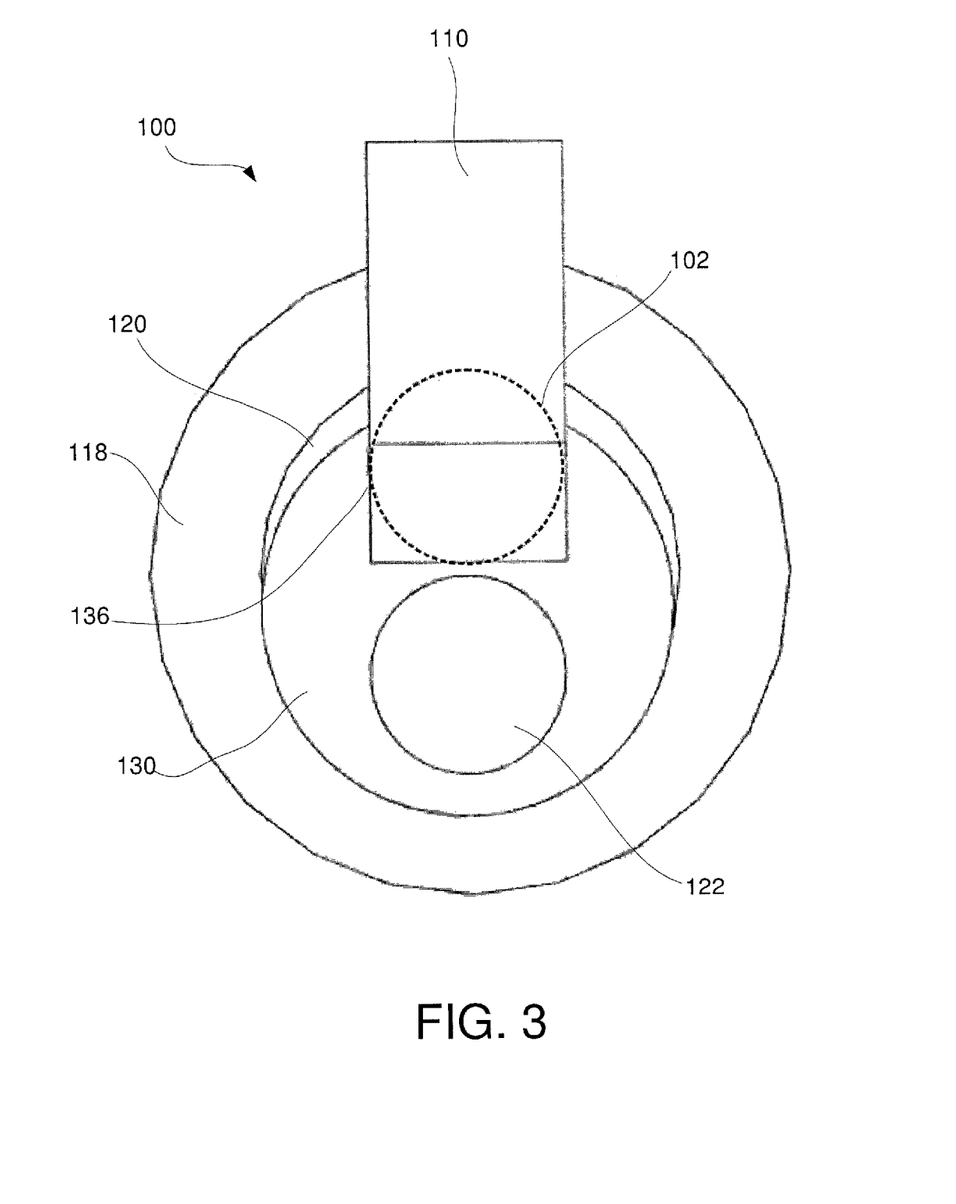
FIG. 3 shows a partial cross-sectional view of the depth gauge of FIG. 1.

As shown in FIGS. 1-3, a probe 100 according to an exemplary embodiment of the invention includes a first rod 102 extending from a proximal end 104 and along an elongated shaft 106 to a distal end 108 including an abutment 110. The abutment 110 is formed with a triangular cross-section, although other shapes may be used without deviating from the scope of the invention. In an exemplary embodiment, a first proximal face 112 of the abutment 110 is substantially planar and extends substantially perpendicular to a longitudinal axis 114 of the first rod 102. As those skilled in the art will understand, this configuration permits the proximal face 112 to be seated substantially flush against an opposing wall of the bone (not shown) in an operative configuration. That is, the proximal face 112 is angled to maximize a contacting surface area thereof with the bone, as will be described in greater detail with respect to the exemplary method below. The proximal face 112 has a substantially rectangular cross-section. A second side wall 116 of the abutment 110 located opposite the lies substantially flush with the rod 102 so that the abutment 110 protrudes transversely away from the rod 102 in only one direction. As those skilled in the art will understand, this configuration permits a physician or other use to control the orientation of the abutment 110 relative to a housing 118 through which the first rod 102 is inserted. The housing 116 is substantially cylindrical and includes a channel 120 extending therethrough. A width of the abutment 110 is selected to be smaller than a diameter of the channel 120 but large enough so that, when the first rod 102 engages an insert 130 of a second rod 122, the abutment 110 extends radially outward beyond the housing 118.

The second rod 122 extends from a proximal end 124 along an elongated shaft 126 to a distal end 128. The distal end 128 includes a substantially cylindrical insert 130 extending along a longitudinal axis 132 offset from a longitudinal axis 134 of the second rod 122, as shown in FIG. 1. The insert 130 further comprises a groove 136 extending longitudinally therethrough, a cross-sectional shape of the groove 136 being substantially cylindrical with a diameter selected to permit slidable insertion of the first rod 102 therein. The groove 136 is open to an opening 138 formed through a side wall of the insert 130. The opening 138 is dimensioned to permit a portion of the first rod 102 to extend thereoutof while preventing the first rod 102 from being dislodged from the groove 136. Specifically, a width of the opening 138 is smaller than a diameter of the first rod 102 to prevent inadvertent movement of the first rod 102 thereoutof. The first rod 102 may be inserted into the groove 136 axially along a longitudinal axis thereof. A distal end of the insert 130 includes an angled wall 140 configured and dimensioned to guide the probe 100 into a bone hole, as will be described in greater detail with respect to the exemplary method below. A spatial orientation of each of the first and second rods 102, 122 and the housing 118 may be controlled by a handle (not shown) employed therewith. The device 100 may be configured for single-use while the handle (not shown) may be used in any plurality of procedures.

Figure 4:
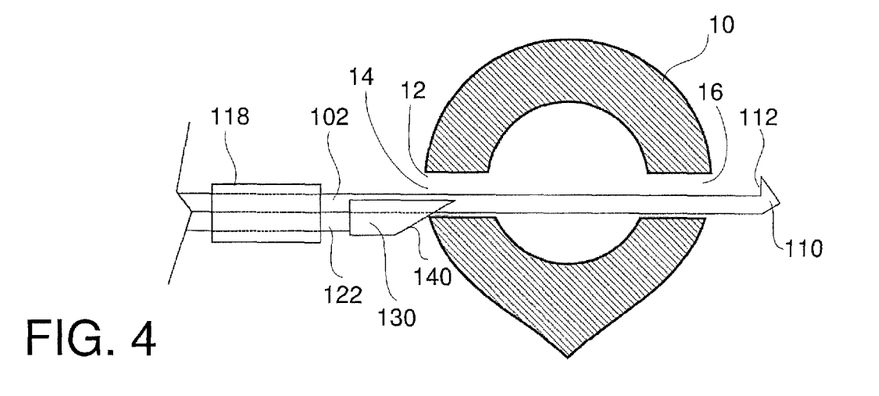
FIG. 4 shows a partial cross-sectional view of the depth gauge of FIG. 1 in a first operative configuration.
Figure 5:
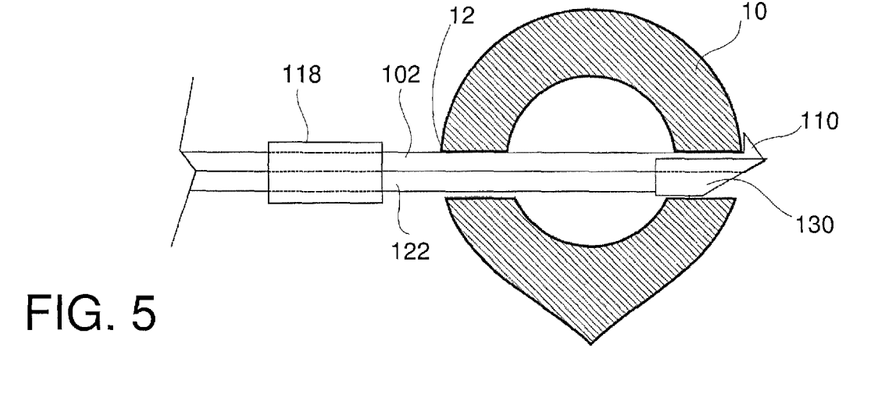
FIG. 5 shows a partial cross-sectional view of the depth gauge of FIG. 1 in a second operative configuration.
Figure 6:
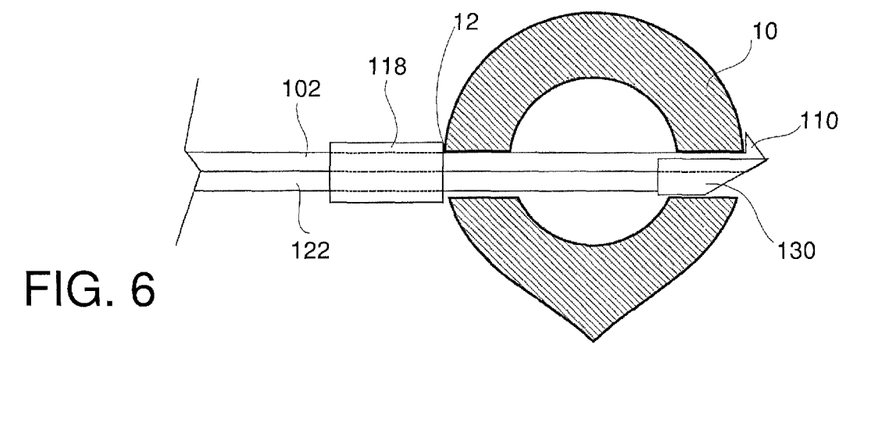
FIG. 6 shows a partial cross-sectional view of the depth gauge of FIG. 1 in a third operative configuration.

FIGS. 4-6 depict an exemplary method for the measurement of a bone hole according to the invention. In first exemplary step, the probe 100 is assembled with the first rod 102 received within the groove 136 of the insert 130. The assembled first and second rods 102, 122 are inserted into the housing 118 with the abutment 110 and insert 130 extending distally beyond the distal end of the housing 118, as shown in FIG. 1. The insert 130 is then positioned against a proximal opening 14 of a bone hole 12 drilled bicortically through a bone 10. The first rod 102 is then advanced distally through the bone until the abutment 110 extends distally out of the bone hole 12 adjacent a distal opening 16 thereof, as shown in FIG. 4. The second rod 122 is then advanced distally through the bone hole 12 as engagement of the angled wall 140 with walls of the bone hole 12 forces an axial alignment of the probe 100 with a central longitudinal axis of the bone hole 12. The second rod 122 is advanced distally relative to the first probe 102 until engagement of the proximal face 112 of the abutment 110 with the distal end 128 of the insert 130 prevents further distal movement thereof. Specifically, the rectangular cross-sectional shape of the proximal face 112 of the abutment is prevented from being inserted into the substantially cylindrical groove 136, which is shown in phantom in FIG. 3. Once the second rod 122 is moved to the configuration of FIG. 5, the first rod 102 is retracted proximally until engagement of the proximal surface 112 with the distal opening 16 of the bone hole 12 prevents further retraction. It is noted that during this step, a distally directed force is maintained on the second rod 122 to maintain a spatial relationship of the first and second rods relative to one another. As shown in FIG. 6, the housing 118 is then advanced distally to contact the proximal opening 14 of the bone hole, allowing a physician or other user to accurately determine the depth of insertion of the probe 100 and thus, the length of the bone hole 12. Specifically, one or both of the first and second rods 102, 122 may be provided with markings (not shown) corresponding to a depth of insertion of the probe 100 into the bone 10. In one non-limiting example, markings on the first or second rods 102, 122 aligned with a proximal end of the housing 118 may indicate the length of the bone hole 12.

To remove the probe 100 from the bone, the distally directed force on the second rod 122 is removed and the second rod 122 moved proximally until the insert 130 has been removed proximally from the bone hole 12. This retraction provides enough open space within the bone hole 12 to permit the abutment 110 to be moved into the bone hole 12 allowing the first rod 102 to be moved proximally out of the bone hole 12 and the removed from the body.

Figure 7:
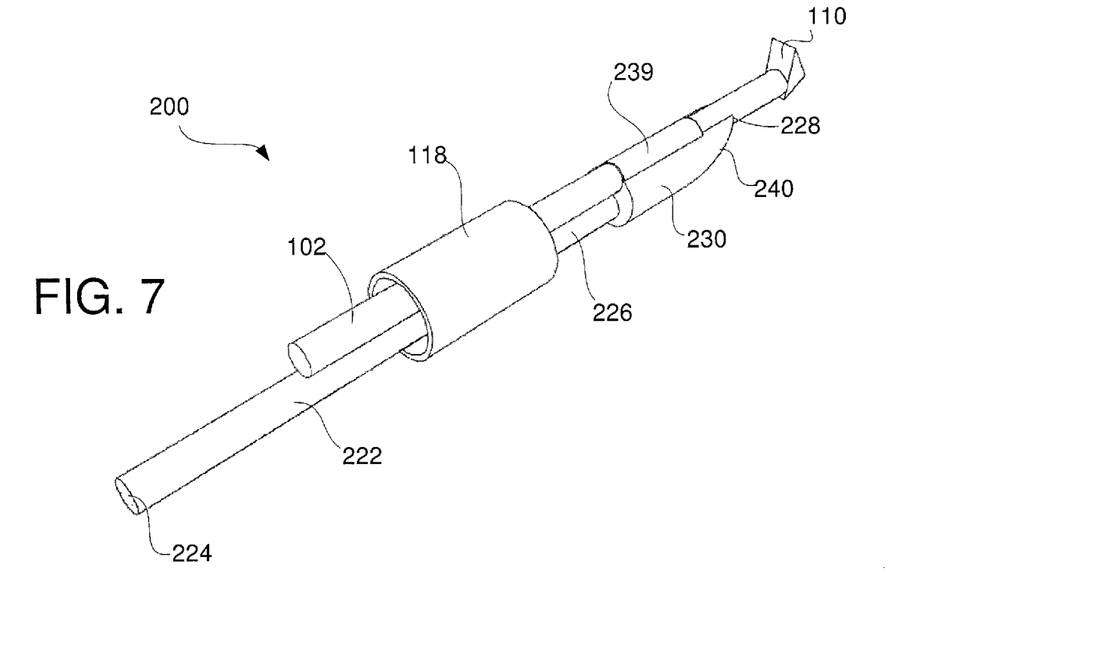
FIG. 7 shows a perspective view of a depth gauge probe according to a first alternate embodiment of the invention.
Figure 8:
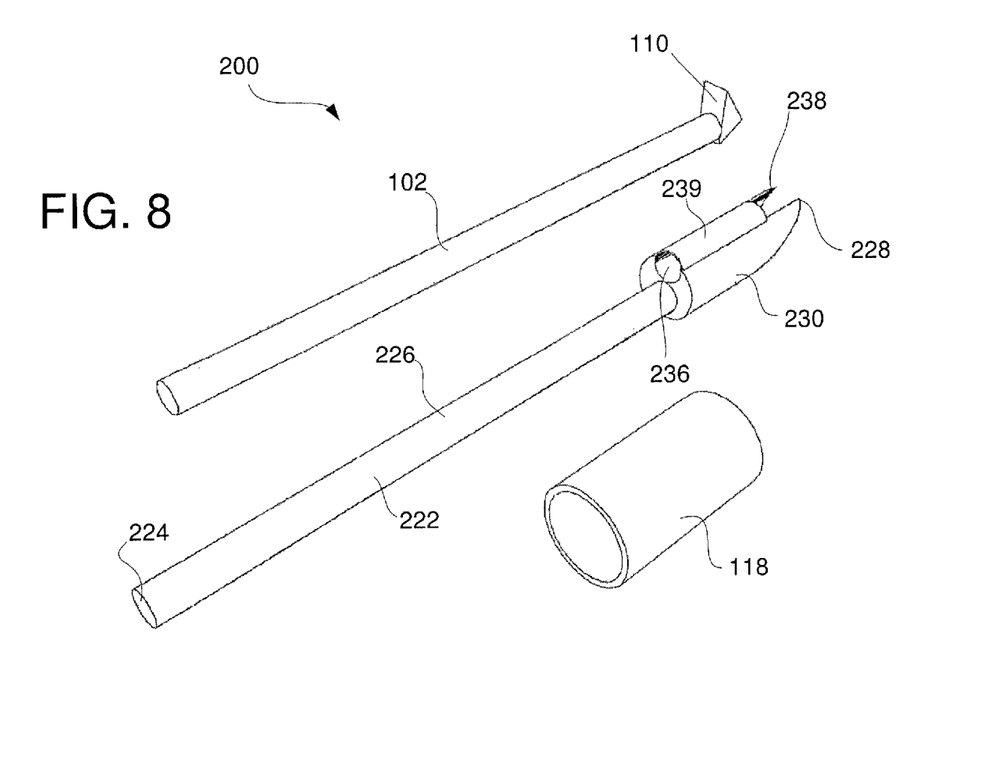
FIG. 8 shows an exploded view of the depth gauge of FIG. 7.
Figure 9:
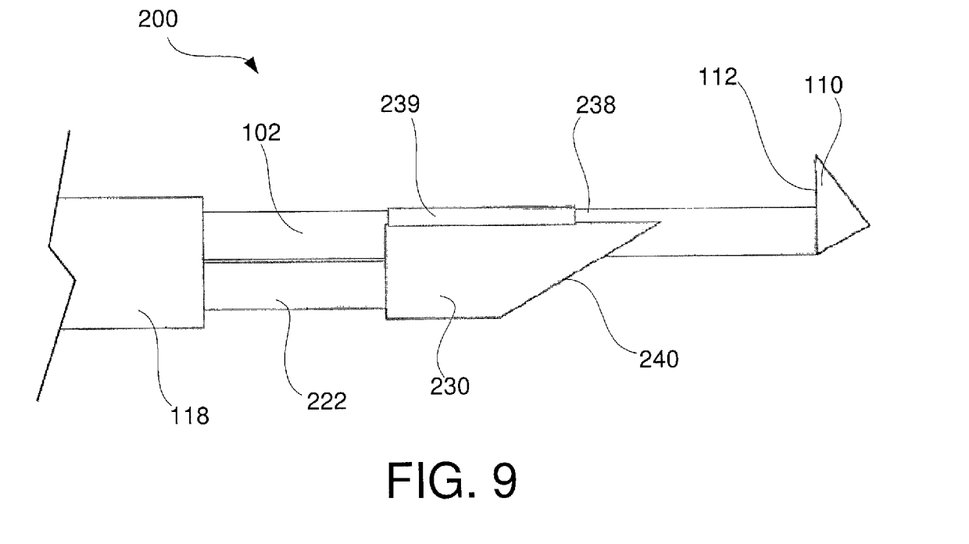
FIG. 9 shows a side view of the depth gauge of FIG. 7.
Figure 10:
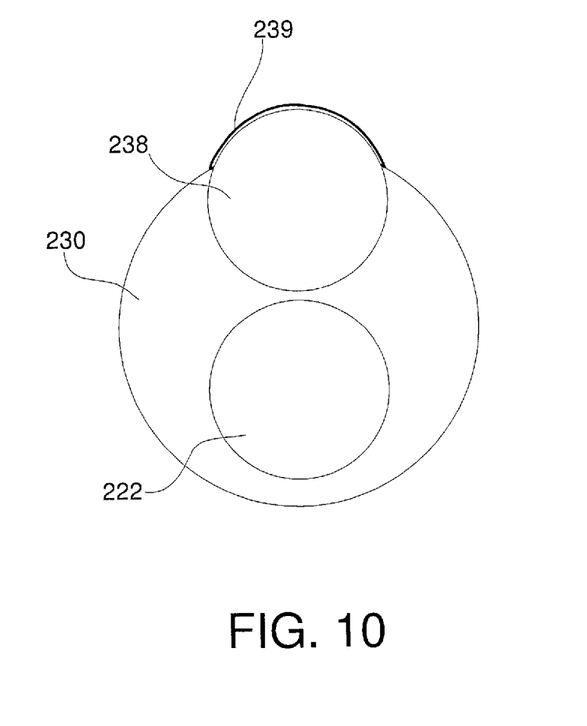
FIG. 10 shows a partial cross-sectional view of an insert of the depth gauge of FIG. 7.

As shown in FIGS. 7-9, a probe 200 according to a first alternate embodiment of the invention is substantially similar to the probe 100 except as noted below, wherein like element have been referenced with like reference numerals. The probe 200 comprises a first rod 102 including an abutment 110 at a distal end thereof and a housing 118. The probe 200 further comprises a second rod 222 substantially similar to the second rod 122 and extending from a proximal end 224 along an elongated shaft 226 to a distal end 228 including an insert 230. The insert 230 includes a groove 236 extending longitudinally therethrough and open to an opening 238. However, a portion of the opening 238 is enclosed by a thin wall 239 configured and dimensioned to prevent inadvertent removal of the first rod 102 out of the groove 236. In this embodiment, the first rod 102 is inserted into the groove 236 by sliding the proximal end 104 thereof axially into the distal end of the groove 236. The wall 239 is formed with a curvature selected to enclose a substantially cylindrical opening having dimensions conforming to dimensions of the shaft 106 of the first rod 102, as shown more clearly in FIG. 10. An exemplary method of use of the probe 200 is substantially similar to that of the probe 100, as described in greater detail earlier.

FIGS. 11-14 depict a probe 300 according to another embodiment of the invention, the probe 300 being formed substantially similar to the probe 100 except as noted below. The probe 300 includes a first rod 302 extending from a proximal end (not shown) along an elongated shaft 306 to a distal end 308 having an abutment 310. The shaft 306 is formed with a substantially cylindrical cross-section, although other cross-sectional shapes may be used without deviating from the scope of the invention. The abutment 310 extends radially away from the first rod 302 in only one direction at an angle extending substantially perpendicular thereto. In an exemplary embodiment, the abutment 310 is integrally formed with the first rod 102. In an alternate embodiment (not shown), the abutment 310 may be formed separately from the first rod 102 and attached thereto using an attachment mechanism known in the art (e.g., welding, adhesive, etc.).

The probe 300 further comprises a second rod 322 formed as an elongated substantially cylindrical element extending from a proximal end (not shown) along a substantially cylindrical shaft 326 to a distal end 328. A channel 324 extends through the second rod 322, the channel 324 being dimensioned to receive the first rod 302 therethrough. A distal end of the second rod includes a recess 330 extending proximally from the distal end 328 by a predetermined distance. The recess 330 permits slidable insertion of the abutment 310 thereinto. At a proximal end, the recess 330 terminates in an angled wall 332 angled to guide insertion of the second rod 322 into the bone hole 12. An outer wall of the second rod 322 opposite the recess 330 includes an increased thickness protrusion 334 extending radially outward from the shaft 326. In an exemplary embodiment, the protrusion 334 has a thickness selected so that a combined diameter of the second rod 322 and the protrusion 334 is substantially equivalent to a thickness of the bone hole 12. As those skilled in the art will understand, this configuration permits the second rod 322 to frictionally engage the bone hole 12 in an operative configuration, as will be described in greater detail with respect to the exemplary method disclosed below. A distal wall 340 of the protrusion 334 is angled to guide insertion of the second rod 322 into the bone hole 12, as described in greater detail in earlier embodiments. Similarly, a proximal wall 342 of the protrusion 334 is also angled to guide removal of the second rod 322 from the bone hole 12.

The probe 300 further comprises a sleeve 318 formed substantially similar to the housing 118. Specifically, the sleeve 318 is substantially cylindrical and includes a substantially cylindrical channel (not shown) extending therethrough, a diameter of the channel being equal to or greater than the combined diameter of the second rod 322 and the protrusion 334.

Figure 11:
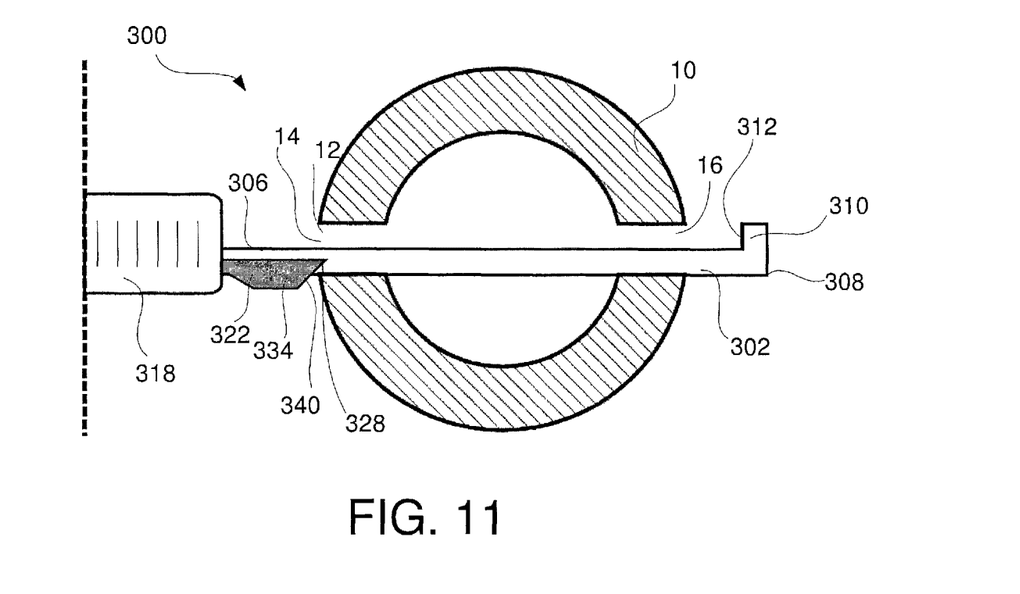
FIG. 11 shows a partial cross-sectional view of the depth gauge according to second alternate embodiment of the invention in a first operative configuration.
Figure 12:
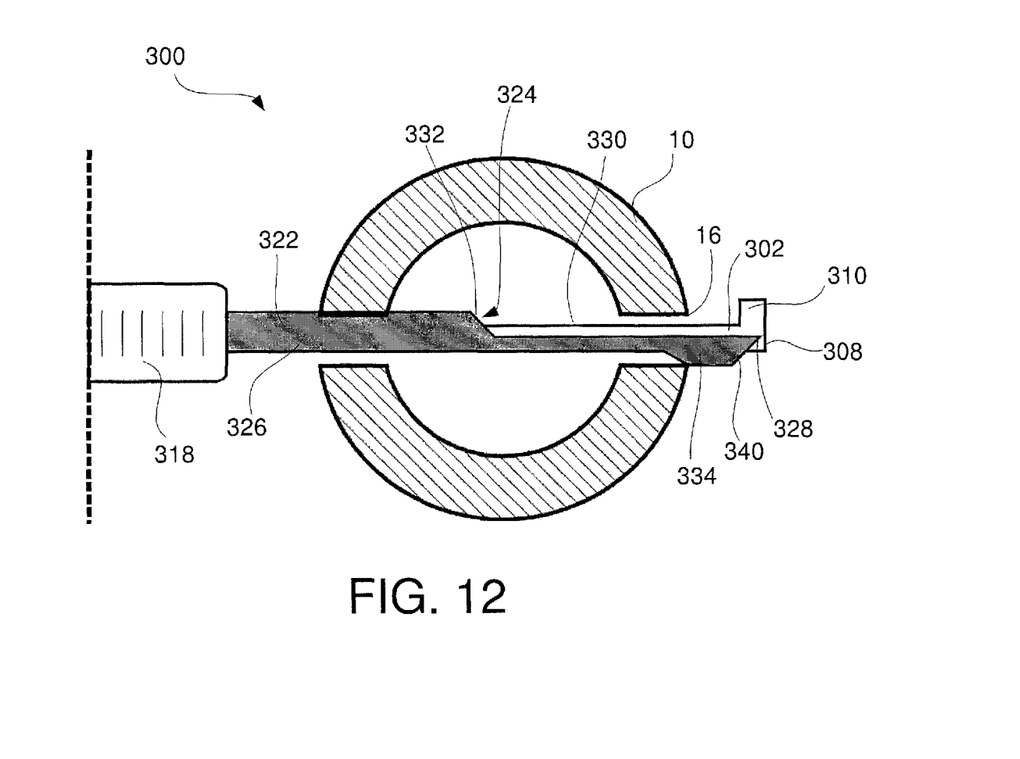
FIG. 12 shows a partial cross-sectional view of the depth gauge of FIG. 11 in a second operative configuration.
Figure 13:
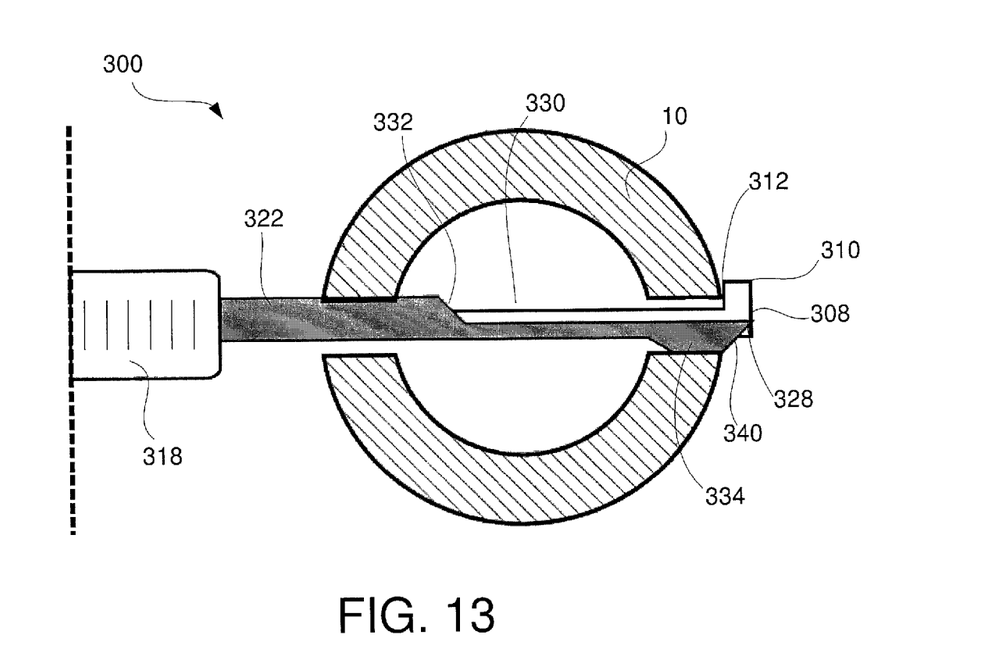
FIG. 13 shows a partial cross-sectional view of the depth gauge of FIG. 11 in a third operative configuration.
Figure 14:
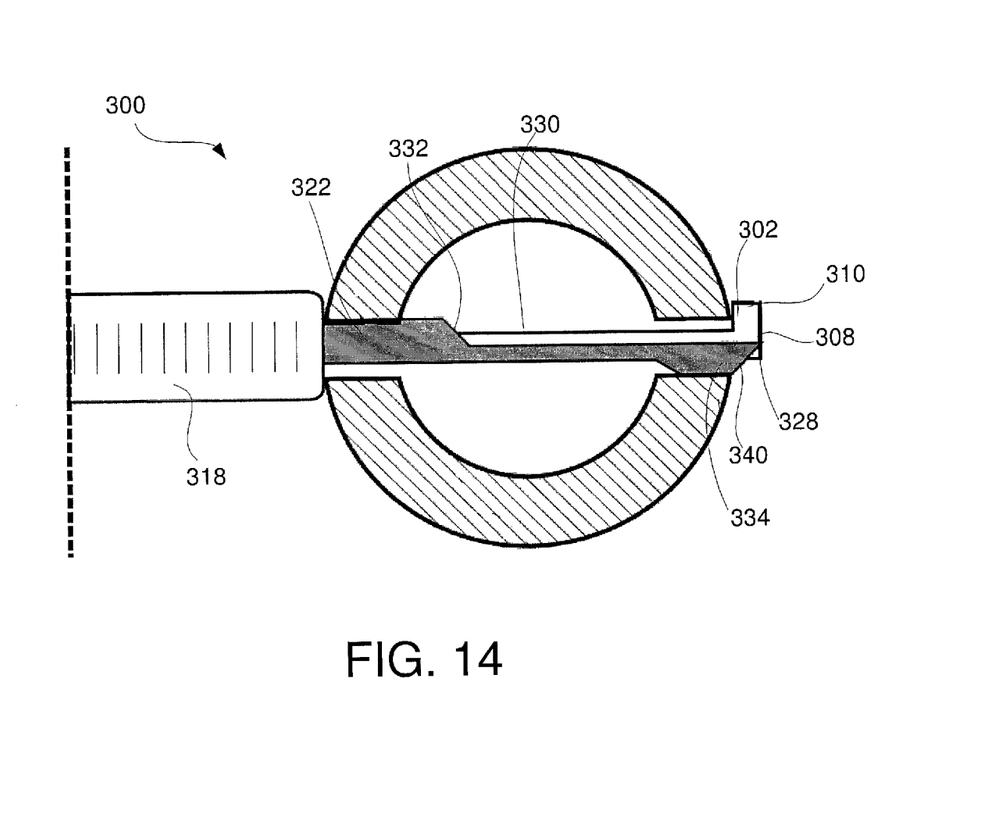
FIG. 14 shows a partial cross-sectional view of the depth gauge of FIG. 11 in a fourth operative configuration.

In accordance with an exemplary method according to the invention, the first rod 302 is first slidably inserted through the channel 324 of the second rod 322. The distal end 328 of the second rod 322 is positioned against the proximal opening 14 of the bone hole 12 while the first rod 302 is moved axially relative thereto into the bone hole 12 until the abutment 310 moves distally of the distal opening 16, as shown in FIG. 11. The second rod 322 is then moved distally relative to the first rod 302 until the protrusion 334 is positioned adjacent to the abutment 310, as shown in FIG. 12. This position is indicated to the physician or other user by a hard stop provided in a handle (not shown) connected to the probe 300. Specifically, the handle (not shown) is configured such that the protrusion 334 of the second rod 322 is incapable of being advanced distally relative to the abutment 310 of the first rod 302. Specifically, in this configuration, the shaft 326 engages the near cortex of the bone hole 12 while the protrusion 334 engages the far cortex of the bone hole 12. This position can be manually verified by advancing the protrusion 334 distally beyond the far cortex until the frictional resistance is removed. The second rod 322 is then moved proximally by a short distance so that the protrusion 334 slides back into the far cortex. As shown in FIG. 13, the second rod 322 is then held in place while the first rod 302 is moved proximally until a proximal face 312 of the abutment 310 engages the distal opening 16 of the bone hole 12, preventing further retraction thereof. As shown in FIG. 14, the sleeve 318 is then advanced distally to contact the proximal opening 14 of the bone hole 12, allowing a physician or other user to accurately determine the depth of insertion of the probe 300 and thus, the length of the bone hole 12, as described in greater detail in earlier embodiments (e.g., via markings).

Figure 15:
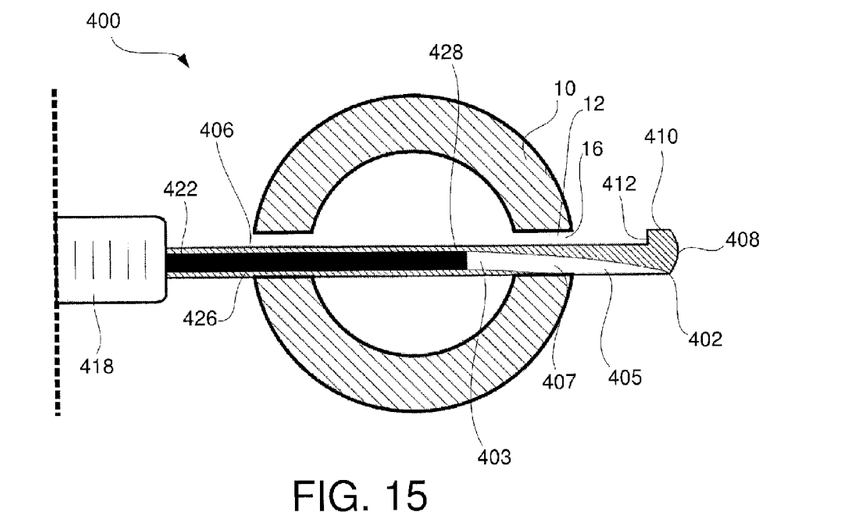
FIG. 15 shows a partial cross-sectional view of a depth gauge according to third alternate embodiment of the invention in a first operative configuration.
Figures 16, 17:
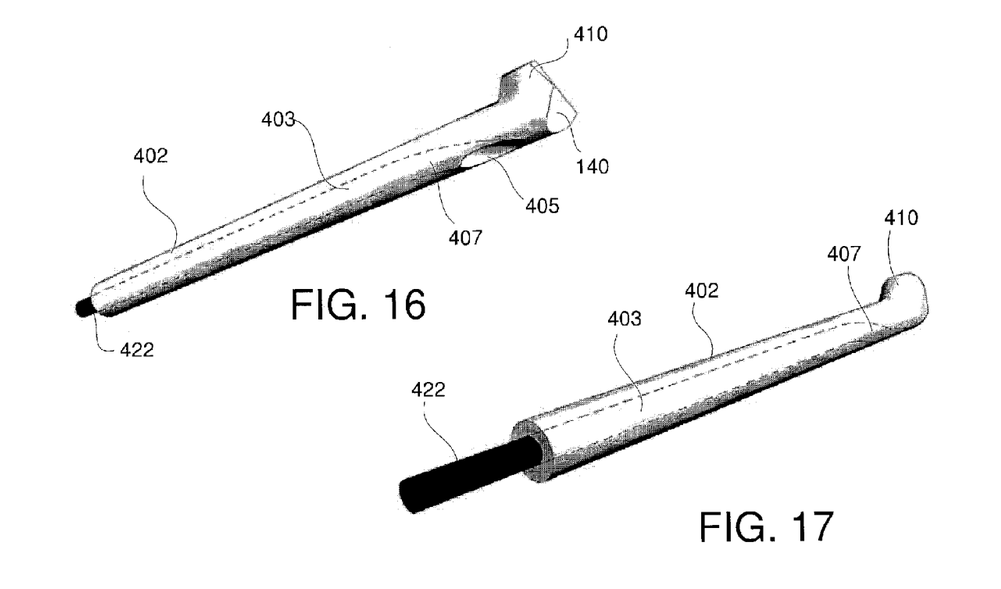
FIG. 16 shows a first perspective view of the depth gauge of FIG. 15.
FIG. 17 shows a second perspective view of the depth gauge of FIG. 15.

FIGS. 15-22 depict a probe 400 according to yet another embodiment of the invention, the probe 400 being formed substantially similar to probes 100, 200, 300 except as noted below. The probe 400 comprises a first rod 402 formed substantially similar to the first rod 102, 202, 302. Specifically, the first rod 402 extends from a proximal end (not shown) and along an elongated shaft 406 to a distal end 408 having an abutment 410 extending substantially perpendicular to a longitudinal axis of the shaft 406. A thickness of the distal end 408 including the abutment 410 is substantially similar to the thickness of the bone hole 12. The first rod 402 further comprises a cylindrical channel 403 extending therethrough and configured to slidably receive a second rod 422 therein, as shown in FIGS. 15-17. The first rod 402 includes an opening 405 positioned near the distal end 408. A ramp 407 extends from the channel 403 to the opening 405 to guide the second rod 422 out of the channel as it is moved distally therepast. The ramp 407 is angled to guide the second rod 422 thereoutof at an angle relative to a longitudinal axis of the first rod 402. Specifically, the ramp 407 is angled so that the second rod 422 is angled away from the first rod 402 in a direction opposite a direction of the abutment 410. Accordingly, as the second rod 422 is moved distally out of the opening 405, the distal end 408 of the first rod 402 is moved radially away from the distal end 428 of the second rod 422.

Figure 18:
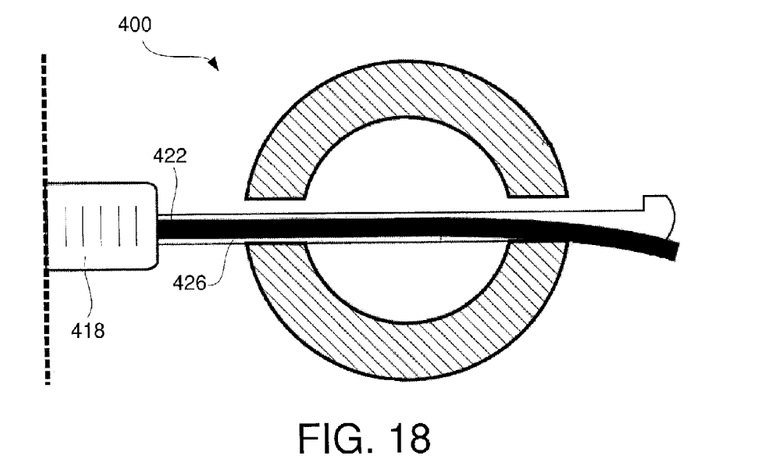
FIG. 18 shows a partial cross-sectional view of the depth gauge of FIG. 15 in a second operative configuration.
Figure 19:
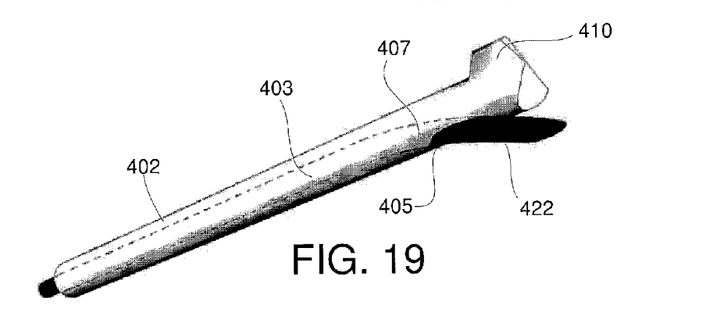
FIG. 19 shows a first perspective view of the depth gauge of FIG. 18.
Figure 20:
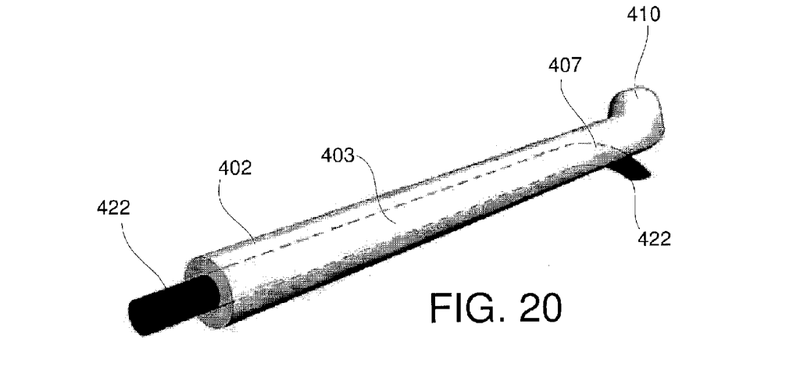
FIG. 20 shows a second perspective view of the depth gauge of FIG. 18.
Figure 21:
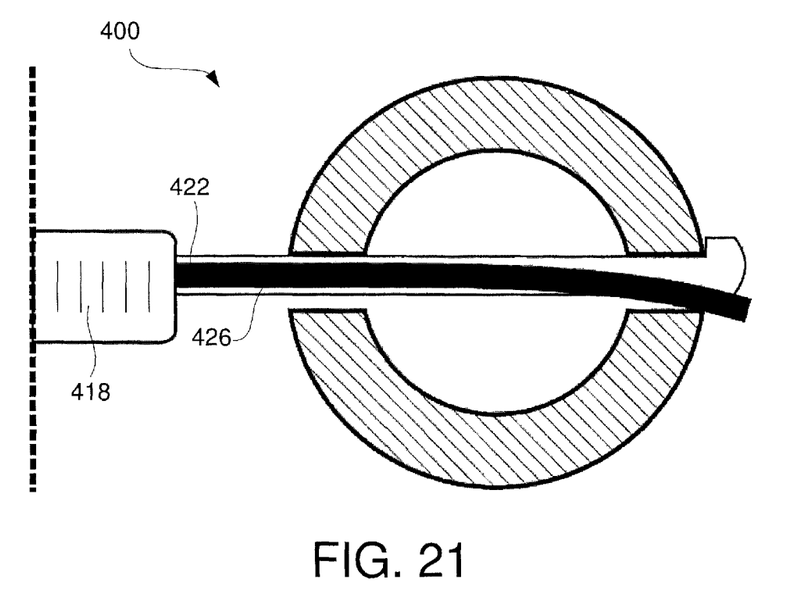
FIG. 21 shows a partial cross-sectional view of the depth gauge of FIG. 15 in a third operative configuration.
Figure 22:
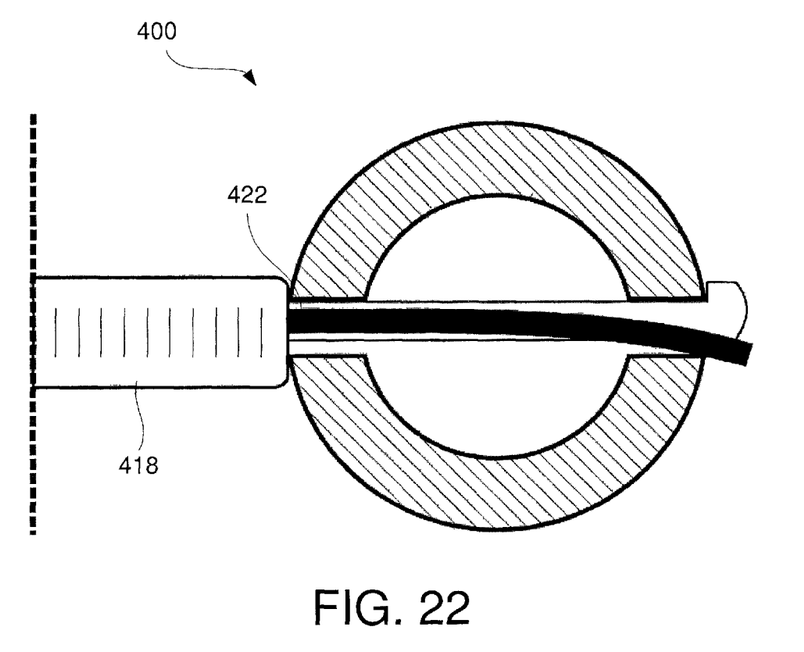
FIG. 22 shows a partial cross-sectional view of the depth gauge of FIG. 15 in a fourth operative configuration.

In accordance with an exemplary method according to the invention, the second rod 422 is slidably inserted through the channel (not shown) of the first rod 402 such that a distal end 424 thereof is located proximally of the opening (not shown). The first rod 402 is then moved axially through a sleeve 418 into the bone hole 12 until the abutment 410 moves distally of the distal opening 16, as shown in FIG. 15. The second rod 422 is then moved distally relative to the first rod 402 until the distal end 424 moved distally out of the opening (not shown) and is guided by the ramp (not shown) and extends distally out of the distal opening 16 of the bone hole 12, as shown in FIG. 16. This positioned is verified to the physician by the hard stop provided in a handle (not shown) connected to the probe 400, as described in greater detail earlier. In this configuration, a combined diameter of distal ends 408, 424 of the first and second rods 402, 422 is greater than the diameter of bone hole, thus preventing retraction of the probe 400 proximally. As shown in FIG. 17, the second rod 422 is then held in place while the first rod 402 is moved proximally until a proximal face 412 of the abutment 410 engages the distal opening 16 of the bone hole 12, preventing further retraction thereof. As shown in FIG. 18, the sleeve 418 is then advanced distally to contact the proximal opening 14 of the bone hole 12, allowing a physician or other user to accurately determine the depth of insertion of the probe 400 and thus, the length of the bone hole 12, as described in greater detail in earlier embodiments (e.g., via markings).

It will be apparent to those skilled in the art that various modifications and variations can be made in the structure and the methodology of the present invention without departing from the spirit or scope of the invention. Thus, it is intended that the present invention cover the modifications and variations of this invention provided that they come within the scope of the appended claims and their equivalents.

What is claimed is:

1. A device for measuring blind holes formed through a bone, comprising:
    a first elongated rod including a shaft extending from a proximal end to a distal end, the distal end including an increased diameter abutment extending radially outward therefrom, the abutment including a proximal surface formed to contact a portion of the bone adjacent a distal opening of the blind hole to assume a locked configuration with the bone; and
    a second elongated rod extending from a proximal end to a distal end along a central longitudinal axis and including a cylindrical insert having a diameter increased relative to a diameter of a proximal portion of the second elongated rod, said cylindrical insert includes a wedge at a distal most end of said second elongated rod, the insert having a groove extending therethrough, the groove being sized and shaped to slidably receive the first rod therethrough, wherein a central longitudinal axis of the insert extends parallel to and is radially offset from the central longitudinal axis of the second elongated rod; and
    a cylindrical housing having a substantially cylindrical channel extending therethrough to slidably receive the first and second elongated rods, wherein one of the first and second elongated rods includes markings indicating a depth of a measured blind hole.

2. The device of claim 1, wherein a longitudinal axis of the groove extends parallel to the longitudinal axis of the second elongated rod.

3. The device of claim 1, wherein a combined diameter of the insert and the shaft of the first rod is substantially equivalent to a diameter of the blind hole.

4. The device of claim 1, wherein the abutment has a triangular cross-section.

5. The device of claim 1, further comprising an opening formed on a side wall of the insert, the opening being open to the groove.

6. The device of claim 5, wherein the groove forms part of a cylinder.

7. The device of claim 6, wherein engagement of the abutment with a distal end of the groove prevents the insert from moving distally relative to the abutment.

8. The device of claim 1, wherein the wedge is configured to guide insertion of the insert into the blind hole.

9. The device of claim 1, wherein the first rod is slidably received within the second rod.

10. The device of claim 1, wherein a proximal end of one of the first and second rods includes the markings indicating a depth of insertion of the device into the blind hole.

11. A system for measuring a depth of a blind hole formed through a bone, comprising:
    a first elongated rod including a shaft extending from a proximal end to a distal end, the distal end including an increased diameter abutment extending radially outward therefrom, the abutment including a proximal surface formed to contact a portion of the bone adjacent a distal opening of the blind hole to assume a locked configuration with the bone;
    a second elongated rod extending from a proximal end to a distal end along a central longitudinal axis, the second elongated rod including a cylindrical insert having a diameter increased relative to a diameter of a proximal portion of the second elongated rod, said cylindrical insert includes a wedge at a distal most end of said second elongated rod, the insert having a groove extending therethrough, the groove being sized and shaped to slidably receive the first rod therethrough, wherein a central longitudinal axis of the insert extends parallel to and is radially offset from the central longitudinal axis of the second elongated rod; and
    a cylindrical housing having a substantially cylindrical channel extending therethrough to slidably receive the first and second elongated rods, wherein one of the first and second elongated rods includes markings indicating a depth of a measured blind hole.

* * * * *